（12）United States Patent
Degala et al.

(10) Patent No.: US 9,757,551 B2
(45) Date of Patent: Sep. 12, 2017

(54) ANTISEPTIC APPLICATOR (71) Applicant: CAREFUSION 2200, INC., San Diego, CA (US)

(72) Inventors: Satish Degala, Arlington Heights, IL (US); Kenneth Bruce Thurmond, II, Deer Park, IL (US); Kenneth Michael Dokken, El Paso, TX (US); Aishwarya Vaidyanathan, Arlington Heights, IL (US); Angel Magallon, El Paso, TX (US); David A. Parrott, Cincinnati, OH (US); Benjamin T. Krupp, Wyoming, OH (US)

(73) Assignee: CAREFUSION 2200, INC., San Diego, CA (US)

( * ) Notice: Subject to any disclaimer, the term of this patent is extended or adjusted under 35 U.S.C. 154(b) by 484 days.

(21) Appl. No.: 14/046,582

(22) Filed: Oct. 4, 2013

(65) Prior Publication Data

US 2015/0098861 A1    Apr. 9, 2015

(51) Int. Cl.
*A61M 35/00* (2006.01)
*A61F 13/40* (2006.01)
*A61L 2/18* (2006.01)

(52) U.S. Cl.
CPC ............ *A61M 35/006* (2013.01); *A61L 2/18* (2013.01)

(58) Field of Classification Search
CPC ................................................. A61M 35/006
See application file for complete search history.

(56) References Cited

U.S. PATENT DOCUMENTS

| 3,757,782 A | 9/1973 | Aiken |
| 4,225,254 A | 9/1980 | Holberg et al. |
| 4,415,288 A | 11/1983 | Gordon et al. |
| 4,498,796 A | 2/1985 | Gordon et al. |
| 5,186,563 A | 2/1993 | Gebhard et al. |

(Continued)

FOREIGN PATENT DOCUMENTS

| WO | WO 00/58164 A1 | 10/2000 |
| WO | WO 2013/047280 A1 | 10/2000 |

OTHER PUBLICATIONS

Jan. 15, 2015 PCT International Search Report and Written Opinion issued in International Patent Application No. PCT/US14/59270.

(Continued)

*Primary Examiner* — Donald Spamer
(74) *Attorney, Agent, or Firm* — Arent Fox LLP (57) ABSTRACT An applicator assembly may include a body having a proximal end portion and a distal end portion, an actuator operatively coupled to the body, a container disposed within the body, an application member attached to the distal end portion, and a valve disposed between the container and the application member. Actuation of the actuator opens the valve and places the interior of the container in fluid communication with the application member by way of a compressive force applied to the body. A method of applying a solution to a surface may include actuating the actuator, wherein actuation of the actuator applies a compressive force to the body that opens the valve and places the interior of the container in fluid communication with the application member, and contacting the application member to the surface, thereby applying the solution to the surface.

24 Claims, 4 Drawing Sheets

(56) References Cited

U.S. PATENT DOCUMENTS

| | | |
|---|---|---|
| 5,288,159 A | 2/1994 | Wirt |
| 5,308,180 A | 5/1994 | Pournoor et al. |
| 5,435,660 A | 7/1995 | Wirt |
| 5,445,462 A | 8/1995 | Johnson et al. |
| 5,509,430 A | 4/1996 | Berger |
| 5,538,353 A | 7/1996 | DeHavilland |
| 5,607,766 A | 3/1997 | Berger |
| 5,620,641 A | 4/1997 | Berger |
| 5,633,082 A | 5/1997 | Berger |
| 5,658,084 A | 8/1997 | Wirt |
| 5,690,958 A | 11/1997 | McGrath |
| 5,769,552 A | 6/1998 | Kelley et al. |
| 5,772,346 A | 6/1998 | Edwards |
| 5,791,801 A | 8/1998 | Miller |
| 5,927,884 A | 7/1999 | Kao |
| 6,103,181 A | 8/2000 | Berger |
| 6,269,821 B1 | 8/2001 | Berke et al. |
| 6,371,675 B1 | 4/2002 | Hoang et al. |
| 6,488,665 B1 | 12/2002 | Severin et al. |
| 6,533,484 B1 | 3/2003 | Osei et al. |
| 6,536,975 B1 | 3/2003 | Tufts |
| 6,576,034 B2 | 6/2003 | Berger |
| 6,616,723 B2 | 9/2003 | Berger |
| 6,916,133 B2 | 7/2005 | Hoang et al. |
| 6,945,722 B2 | 9/2005 | Colburn et al. |
| 6,991,393 B2 | 1/2006 | Tufts et al. |
| 6,991,394 B2 | 1/2006 | Tufts et al. |
| 7,182,536 B2 | 2/2007 | Tufts et al. |
| 7,201,525 B2 | 4/2007 | Mohiuddin |
| 7,241,065 B2 | 7/2007 | Tufts et al. |
| 7,422,388 B2 | 9/2008 | Tufts et al. |
| 7,866,471 B2 | 1/2011 | Callahan et al. |
| 7,866,907 B2 | 1/2011 | Cable, Jr. et al. |
| 7,946,779 B2 | 5/2011 | Kaufman et al. |
| 8,118,766 B2 | 2/2012 | Davis et al. |
| 2002/0076258 A1 | 6/2002 | Crosby et al. |
| 2004/0179888 A1 | 9/2004 | Tufts et al. |
| 2006/0039742 A1 | 2/2006 | Cable, Jr. et al. |
| 2006/0065677 A1 | 3/2006 | Py et al. |
| 2006/0252849 A1* | 11/2006 | Rose .................. C09D 5/1668 523/122 |
| 2007/0231051 A1 | 10/2007 | Flores et al. |
| 2007/0248399 A1 | 10/2007 | Tufts et al. |
| 2008/0219750 A1 | 9/2008 | Siegel |
| 2008/0292383 A1 | 11/2008 | Tufts et al. |
| 2008/0298879 A1 | 12/2008 | Chesak et al. |
| 2010/0168636 A1 | 7/2010 | Allard |
| 2010/0168637 A1 | 7/2010 | Casey et al. |
| 2010/0168638 A1 | 7/2010 | Korogi et al. |
| 2010/0286637 A1 | 11/2010 | Cable, Jr. et al. |
| 2011/0066121 A1 | 3/2011 | Hoang et al. |
| 2011/0245784 A1 | 10/2011 | Johnson |
| 2011/0319842 A1 | 12/2011 | McDonald et al. |
| 2012/0003029 A1 | 1/2012 | Guzman et al. |
| 2013/0141186 A1 | 6/2013 | Nguyen et al. |

OTHER PUBLICATIONS

Supplementary Partial European Search Report issued in European Patent Application No. 14850594 dated May 16, 2017.

* cited by examiner

ANTISEPTIC APPLICATOR

BACKGROUND

Field

The present disclosure relates to an antiseptic applicator and method of use thereof, and more particularly, to an antiseptic applicator that uses a compressive force to actuate release of a sealed solution, preferably an antimicrobial solution, from a container.

Description of Related Art

Antiseptic applicators for the preparation of a patient prior to surgery, for example, are known and common in the prior art. Conventional applicators rely on various means of actuation to release a self-contained reservoir of antimicrobial solution for sterilization of the patient's skin. For example, a number of applicators are designed with a puncturing means. These applicators typically include a head with a spike, for example, and a sealed container or cartridge. A push or screw motion is employed to axially translate the head toward the sealed container so that the spike may pierce the sealed container and effectuate the release of the solution contained therein. Some examples of applicators using a puncturing means include U.S. Pat. Nos. 4,415,288; 4,498,796; 5,769,552; 6,488,665; and 7,201,525; and U.S. Pat. Pub. No. 2006/0039742.

Other conventional applicators rely on fracturing an internally situated frangible container or ampoule through the application of a one-way directional force or a localized application of pressure. The directional force is typically applied longitudinally to one end of the ampoule by a pushing motion designed to force the ampoule to fracture under a compressive stress, sometimes at a predetermined area of stress concentration. Alternatively, a pressure may be applied to a localized section of the ampoule through a squeezing motion designed to crush a section of the frangible ampoule in order to release the antimicrobial solution contained therein. Some examples of applicators using frangible ampoules in the manner discussed above include U.S. Pat. Nos. 3,757,782; 5,288,159; 5,308,180; 5,435,660; 5,445,462; 5,658,084; 5,772,346; 5,791,801; 5,927,884; 6,371,675; and 6,916,133. All of the above listed Patent Application Publication and U.S. patents are hereby expressly incorporated by reference herein.

However, in the above-listed applicators, once the fluid is released from the container, there is no mechanism to control the flow of antiseptic solution to the surface (e.g., skin of a patient). Thus, there is a need in the art for an antiseptic applicator that allows for convenient and ergonomic control of the flow of antiseptic solution after the antiseptic fluid has been released from the container or ampoule.

SUMMARY

In accordance with aspects of the present invention, an applicator assembly may include a body having a proximal end portion and a distal end portion, an actuator operatively coupled to the body, a container disposed within the body, an application member attached to the distal end portion, and a valve disposed between the container and the application member. Actuation of the actuator opens the valve and places the interior of the container in fluid communication with the application member by way of a compressive force applied to the body In accordance with aspects of the present invention, a method of applying a solution to a surface may include providing an applicator assembly having: a body having a proximal end portion and a distal end portion, an actuator operatively coupled to the body, a container disposed within the body, an application member attached to the distal end portion, and a valve disposed between the container and the application member, actuating the actuator, wherein actuating the actuator applies a compressive force to the body that opens the valve and places the interior of the container in fluid communication with the application member, and contacting the application member to the surface, thereby applying the solution to the surface.

It will become readily apparent to those skilled in the art from the following detailed description, wherein it is shown and described only exemplary configurations of an applicator assembly. As will be realized, the invention includes other and different aspects of an applicator and assembly and the various details presented throughout this disclosure are capable of modification in various other respects, all without departing from the spirit and scope of the invention. Accordingly, the drawings and the detailed description are to be regarded as illustrative in nature and not as restrictive.

DETAILED DESCRIPTION

Various aspects of an antiseptic applicator may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present.

Relative terms such as "lower" or "bottom" and "upper" or "top" may be used herein to describe one element's relationship to another element illustrated in the drawings. It will be understood that relative terms are intended to encompass different orientations of an antiseptic applicator in addition to the orientation depicted in the drawings. By way of example, if an antiseptic applicator in the drawings is turned over, elements described as being on the "bottom" side of the other elements would then be oriented on the "top" side of the other elements. The term "bottom" can therefore encompass both an orientation of "bottom" and "top" depending on the particular orientation of the apparatus.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of an antiseptic applicator disclosed herein.

The term "about" as used herein means±10%, more preferably ±5%, and still more preferably ±1% of the provided value.

Figure 1:
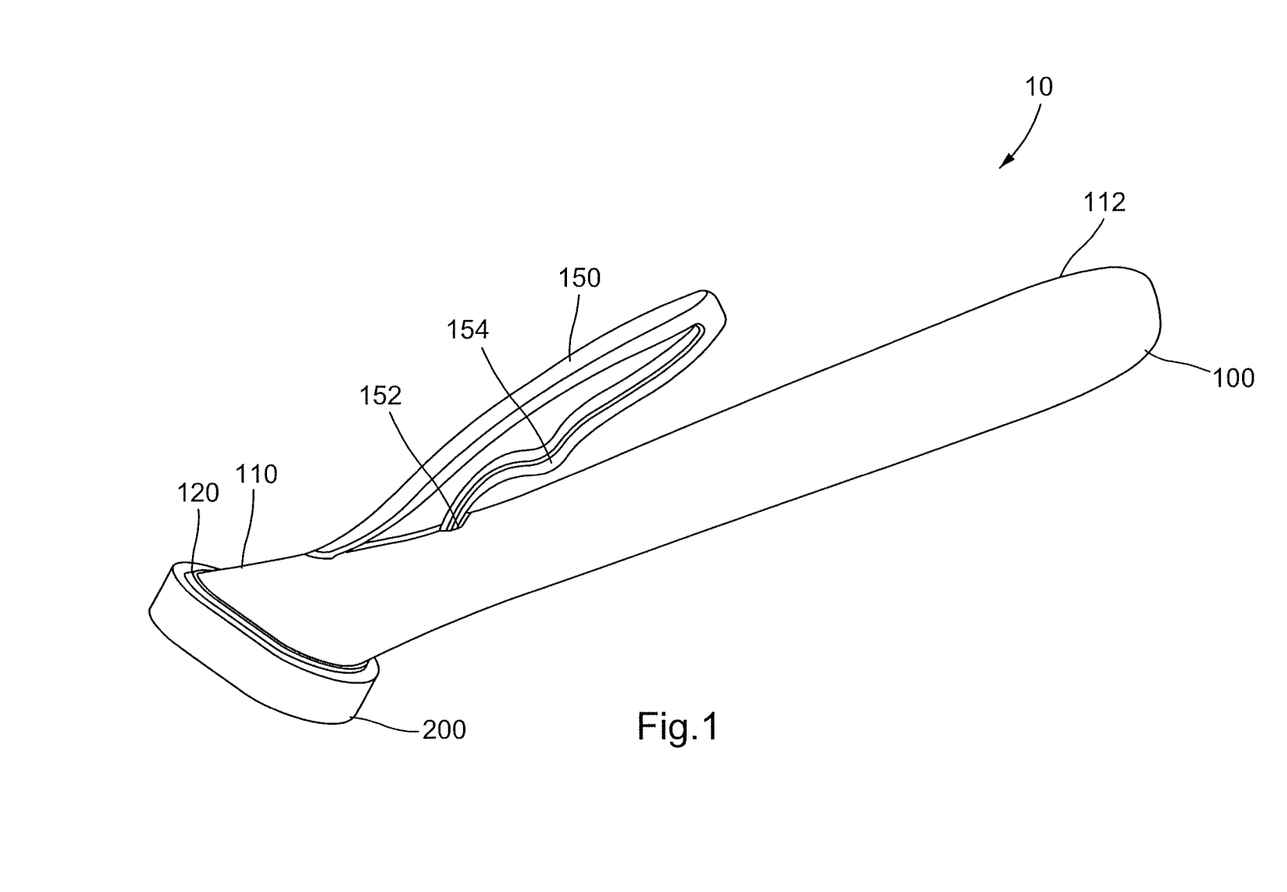
FIG. 1 is a perspective view of an antiseptic applicator, in accordance with certain aspects of the present invention.
Figure 2:
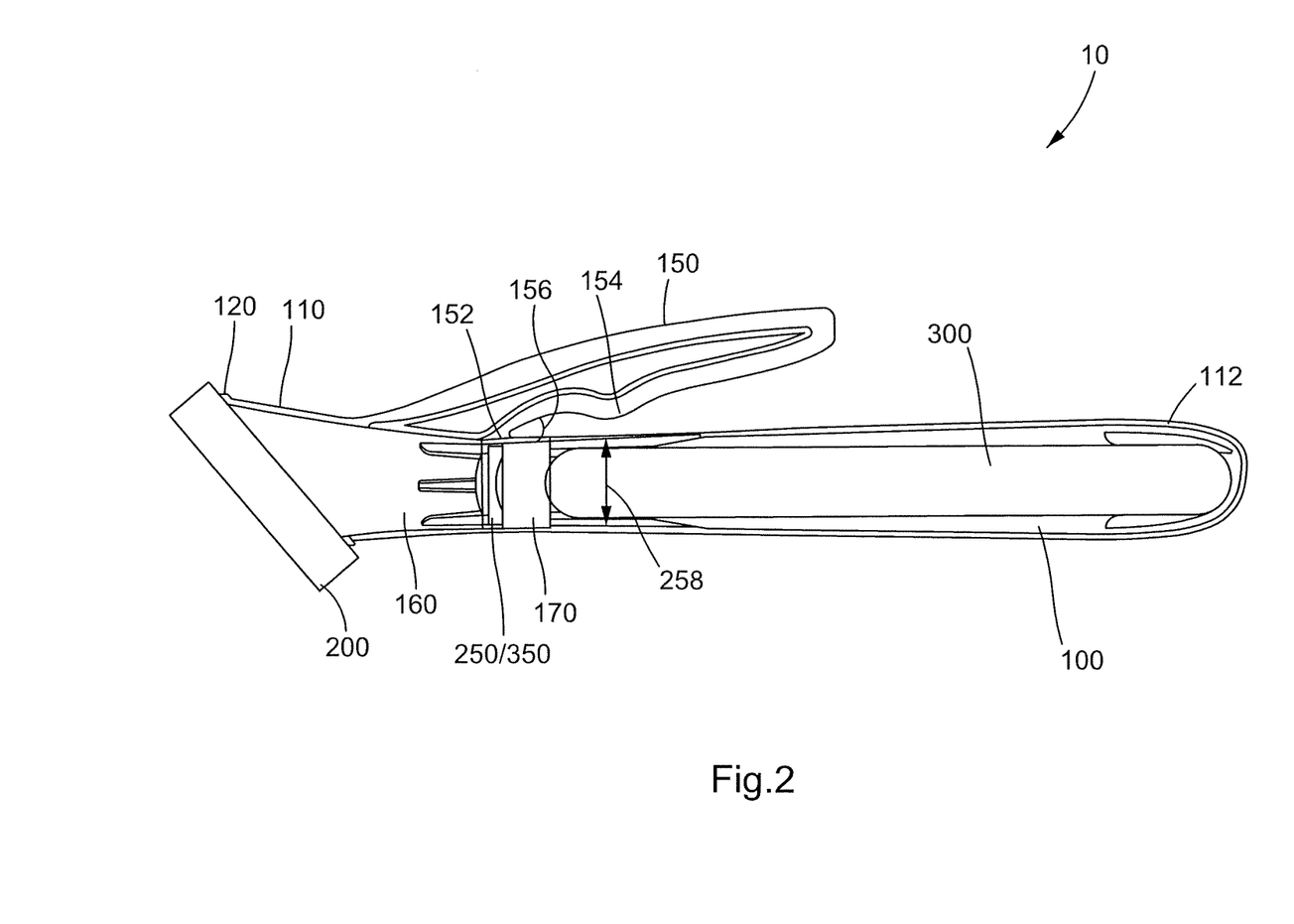
FIG. 2 is a cross sectional view of the antiseptic applicator of FIG. 1.

As shown in FIGS. 1 and 2, an antiseptic applicator 10 may comprise a substantially hollow body 100, which may be cylindrical in shape, an application member 200 mounted to a distal end portion 110 of the body 100, and a solution container 300 received within the body 100. The solution container 300 may be cylindrical or tubular in shape to position the container concentrically into the body 100. In other aspects of the present invention, the body may be any variety of shapes and the container can be any variety of shape that corresponds to (e.g., is congruent to) the particular shape of the body. In an aspect of the present invention the applicator body may be formed of a single piece or it may be made of multiple pieces combined together.

The application member 200 may be formed from a foam sponge material, for example, or any suitable material that allows the controlled application of the contained solution from the solution container 300 to a surface external to the applicator 10. The material chosen may be porous with a particular soak rate, for example, or may be provided with structural features, including slits or apertures, to direct and control the flow rate of the solution through the application member 200. The body 100 may be configured to have a mounting flange 120 at the distal end portion. The mounting flange provides a surface for affixing the application member 200 to the body 100. In an aspect, the foam may be attached in any acceptable manner known in the relevant art, such as providing a novonette backing to the application member, which allows the application member to be ultrasonically welded to the body of the applicator.

The solution container 300 is preferably a self-contained structure, formed of a suitable material that is fracturable upon application of sufficient force, e.g., an ampoule. The terms "container" and "ampoule" are used interchangeably herein. Preferably, the container is formed of glass, although other materials are within the scope of the present invention. The wall of the container is of a thickness sufficient to contain the desired liquid during transport and storage, yet allow the container to be fractured upon the application of localized pressure. The container 300 may contain medicaments, chemical compositions, cleansing agents, cosmetics, or the like. For example, the container 300 may be filled with antiseptic compositions (e.g., compositions comprising one or more antiseptic molecules) preferably an antimicrobial liquid or gel composition, such as a chlorhexidine gluconate solution or a povidone iodine (PVP-I) alcohol gel solution, for antiseptic application to a patient prior to surgery. The container 300 is designed to withstand various heat and chemical sterilization techniques, which may be performed sequentially with a solution filling process, in accordance with techniques that are well known in the art.

The antiseptic solution may comprise an alcoholic solvent. For example, the alcoholic solvent may be selected from the group consisting of ethanol, isopropanol, and n-propanol. The amount of solvent may be from about 40% v/v to about 90% v/v, more preferably about 50% v/v to about 80% v/v, and still more preferably about 60% v/v to about 70% v/v.

The container may contain antiseptic solution of a sufficient amount to be applied to a desired surface and have an antimicrobial effect on the desired surface. In one aspect, the desired surface is a patient's skin. It will be appreciated that the amount of antiseptic solution needed to have an antimicrobial effect on a desired surface to which the antiseptic is applied may vary. In one aspect the amount of antiseptic solution needed is 0.01-100 ml of antiseptic. More preferably, the amount of antiseptic solution need is about 0.5-60 ml and still preferably about 0.5-30 ml. Examples include 0.67, 1.0, 1.5, 3.0, 10.5, and 26.0 ml of antiseptic. However, it will be appreciated that any amount that has an antimicrobial effect on a desired surface may be utilized with the liquid applicator and method.

Suitable antiseptic molecules include bis-(dihydropyridinyl)-decane derivatives, octenidine salts, cationic surfactants, biguanides, and generally cationic antiseptic molecules. Preferred antiseptic agents include octenidine dihydrochloride and chlorhexidine gluconate. The concentration of the cationic antiseptic in hydroalcoholic solution may vary depending on the specific cationic antiseptic species used or the desired antimicrobial effect that is desired. For example, when using octenidine dihydrochloride or an octenidine salt the concentration may vary from about 0.0001% w/v to about 2.0% w/v, more preferably from about 0.01% w/v to about 0.5% w/v, and still more preferably from about 0.1% w/v to about 0.4% w/v. When chlorhexidine or a chlorhexidine salt is used, the concentration may be from about 0.1% w/v to about 2.5% w/v, more preferably from about 0.5% w/v to about 2.25% w/v, and still more preferably about 1.2% w/v to about 2.0% w/v.

Body 100 also includes an actuator 150. Actuator 150 may be any mechanism configured such that, when actuated, fractures the container 300 and also opens a valve, as described in detail below. In an aspect of the present invention the actuator 150 may be a lever. As shown in FIGS. 1 and 2 the actuator 150 may project from the top portion of body 100. However, it will be appreciated that actuator 150 may project from any portion of body 100. The actuator 150 may include a first contact point 152 and a second contact point 154, which apply compressive force to the body 100 when the actuator 150 is actuated. The actuator 150 may extend at an angle 156 toward the proximal end 112 of the body 100 (e.g., the free end of the actuator may be located closer to the proximal end of the body than the portion of the actuator connected to the body) such that when the lever is actuated (i.e., pressed toward the body 100), the first contact point 152 applies compressive pressure to the body 100 followed by the second contact point 154 applying compressive pressure to the body 100. In another aspect of the present invention, the actuator and the first and second contact points may be configured (e.g., positioned and angled) such that, upon actuation of the actuator, the first and second contact points contact the body contemporaneously or simultaneously. The angle 156 may be from about 1° to about 60°, more preferably from about 5° to about 40°, more preferably from about 10° to about 30°, and still more preferably about 12° to about 18°. The actuation of the actuator 150 is described in more detail below.

With the container 300 concentrically mounted in the body 100, as described above, and the application member 200 mounted to close off the distal end portion 110 of the body 100, a fluid chamber 160 may be formed that extends between the application member 200 and the container 300. A fluid metering device, such as a pledget 170, for example, may be provided in the fluid chamber 160 to further control and/or direct the flow of solution from the container 300 when the assembly 10 is in use. In accordance with another aspect of the present invention, the pledget 170 may tint the solution as the solution flows from the container 300 to the application member 200.

In an aspect of the present invention, the pledget 170 may provide enhanced flow control and tinting of the solution as it flows from the container 300 into the pledget 170. The pledget may comprise a polyolefin fiber matrix, such as Filtrona Porous Technologies part #X6027. The fiber matrix may comprise a homogeneous mixture of bicomponent and monocomponent fibers wherein the monocomponent fibers are formed of the core-forming polymer of the bicomponent fibers, as described in detail in U.S. Pat. Nos. 6,103,181; 6,576,034; 6,616,723; 5,633,082; 5,620,641; 5,607,766; and 5,509,430, each of which are incorporated by reference herein. Altering the material composition will alter material properties such as fluid adsorption and flow rate. Additionally, altering the fiber density will also alter the properties such as flow, porosity, and adsorption. An example fiber density may be about 0.5 g/cc. Higher fiber density increases residence time for the antiseptic solution which increases the intensity of color. In an aspect of the present invention, any suitable hydrophobic polymer material that allows for the flow of a hydroalcoholic solvent may be used. For example, the polymer may be a non-woven polyester.

The pledget 170 may have a dye incorporated therein so that the antiseptic solution becomes tinted as it passes through the pledget. Preferably, the impregnated dye is anionic in nature. The anionic dye may be any suitable dye approved by the FDA and international authorities for use in food, drugs, and/or cosmetics (e.g., D&C and FD&C dyes). Preferred dyes may be selected from the group consisting of FD&C Blue No. 1 (Brilliant Blue FCF), FD&C Blue No. 2 (Indigo Carmine), FD&C Green No. 3 (Fast Green FCF), FD&C Red No. 3 (Erythrosine), FD&C Red No. 40 (Allura Red), FD&C Yellow No. 5 (Tartrazine), FD&C Yellow No. 6 (Sunset Yellow FCF), D&C Yellow No. 8 (Fluorescein), D&C Orange No. 4, D&C Yellow 10 (Quinoline Yellow WS), D&C Yellow No. 11, D&C Red No. 30, and combinations thereof. Other suitable dyes include beta-carotene, curcumin, iron oxide yellow, and riboflavin, iron oxide red, chlorophyll, and the like. Two or more anionic dyes may also be combined and used together. For example, by combining D&C Yellow No. 8 and FD&C Red No. 40 mixed in a 80%/20% w/w basis, an orange tint is produced. Ratios of yellow to red dye may be from 1%:99% w/w to 99%:1% w/w. Additionally, it has been found that when combinations of dyes are incorporated into the pledget, a color change is observed in the antiseptic solution after it is applied to a surface. In particular, because of solubility differences, a particular dye having less solubility will take longer to solubilize in the antiseptic solution. The more soluble color will be exhibited first, then, over time, the less soluble color will be mixed with the more soluble color and a new color will be exhibited as the solution dries. For example, it has been found that when a blend of more than 50% w/w D&C Yellow No. 8 with FD&C Red No. 40 is used, the antiseptic solution initially has a yellow color, which changes gradually to orange over time as the red dye is solubilized and mixed with the yellow dye. During a typical application of the above yellow/red blend, the applied antiseptic solution will start out yellow, turn orange, and then finally dark orange within a short period of time, such as on the order of less than 10 seconds as the solution dries on the skin. In particular, as the solution dries, the deposited dye and drug molecules remain (together referred herein as "the deposit") on the skin surface. The color exhibited by these molecules will change as the solution continues to dry. Thus, in the yellow/red blend, the solution starts out yellow, and as the solution dries and the concentration of the dyes and drug (i.e., the deposit) increase relative to the solvents, the skin surface will turn light orange and then ultimately appear dark orange once dried. The time will vary based on particular fiber density, selected dye(s), and relative amount of particular dyes within the blend of dyes when a blend is used. This color-changing aspect allows the practitioner to visually confirm that the antiseptic solution has dried on the surface. Another example blend comprises Yellow 10 and Red 40, which may be used together in the same ratio as provided above with respect to the blend of Yellow 8 and Red 40.

The applicator 10 may include a valve 250 disposed within fluid chamber 160 and downstream of the pledget 170. The valve 250 may include a slit 252 separating the valve into two opposing portions 251, 253. Thus, the valve 250 is bifurcated. The valve 250 allows reduction of flow rate without entirely stopping the flow, which is described in more detail below. The valve 250 may be positioned within the fluid chamber 160 such the valve 250 contacts the portion of the tube 100 that receives compressing pressure from the first contact point 152 of the lever 150 when the lever 150 is actuated. In another aspect of the present invention, the valve 250 may be disposed sufficiently close to the portion of the tube 100 that receives the compressing pressure from the first contact point 152 so that the valve 250 experiences the compressing force from the first contact point 152. For example, the valve 250 may be disposed within about 7 mm, more preferably within about 4 mm, and still more preferably within about 2 mm of the portion of the tube 100 that receives the compressing pressure from the first contact point 152. When the valve 250 is positioned in the above-described manner, the compressive force applied to the body 100 via the first contact point is transferred to the valve 250.

Figure 3A:
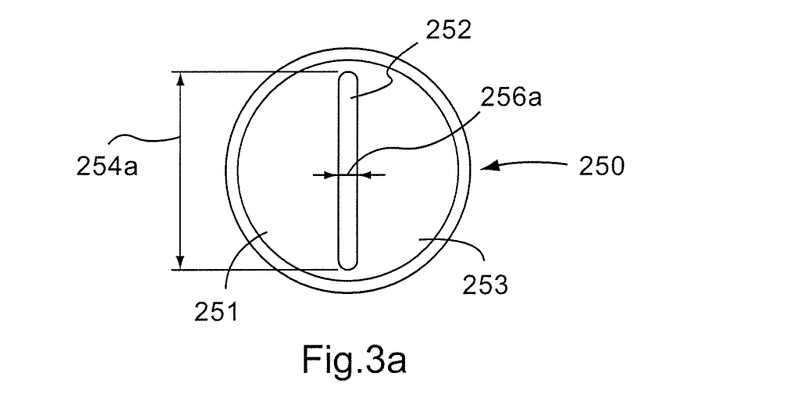
FIG. 3A is a front view of a valve in an pre-actuated configuration, in accordance with certain aspects of the present invention.
Figure 3B:
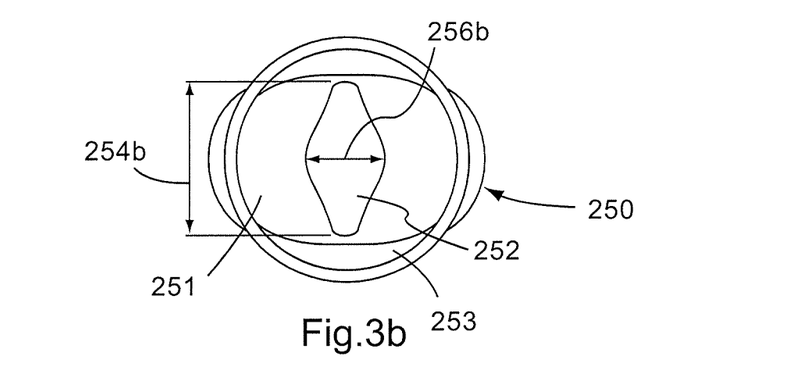
FIG. 3B is a front view of the valve of FIG. 3A in an actuated configuration.
Figure 3C:
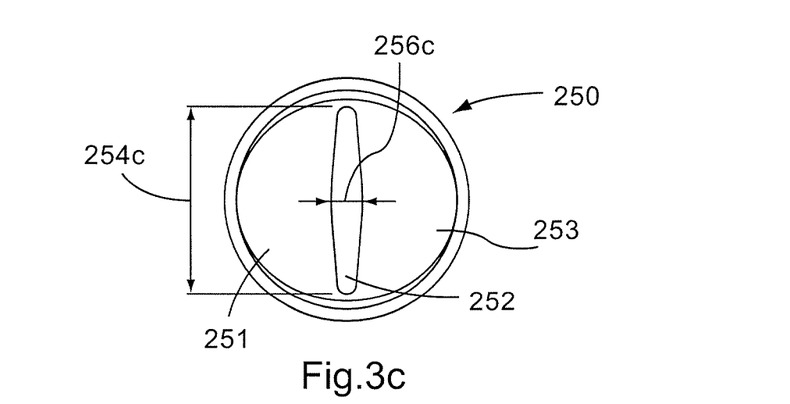
FIG. 3C is a front view of the valve of FIG. 3A in a released configuration.

The valve 250 may be configured to open when pressure is applied to the outer circumference of the valve 250. The valve 250 is shown in detail in FIGS. 3A-3C. FIGS. 3A-3C show front views of the valve 250 (i.e., the views show the surface of the valve that faces the application member 200). FIG. 3A shows a front view of the valve 250 prior to actuation of the actuator 150, i.e., prior to the application of any compressive force. FIG. 3B shows a front view of the valve 250 during maximum actuation of the actuator 150, i.e., during maximum application of compressive force. FIG. 3C shows a front view of the valve 250 after actuation of the actuator 150 has been discontinued, i.e., when the compressive force has been removed.

As shown in FIGS. 3A-3C the slit 252 may extend substantially vertically within the body 100, i.e., perpendicular to a longitudinal axis of the body 100 along the height of the body 100. In other words, when looking at a face of the valve 250 when the applicator is oriented such that the actuator extends from the top of the applicator (i.e. the orientation shown in FIG. 2), the slit 252 may extend from in a straight line from the 12 o'clock position to the 6 o'clock position. The slit 252 may be angled up to ±15° from the 12 o'clock/6 o'clock position, more preferably up to ±10°, still more preferably ±5°, and most preferably ±1°. In the pre-actuated configuration shown in FIG. 3A, the slit may have a substantially uniform height 254a and a substantially uniform width 256a. The height 254a of the slit 252 in the pre-actuated state may be about or near equal to the height of body 100. For example, the ratio of the height 254a of the slit 252 to the height 258 of the body 100 may be from about 0.7:1 to about 1:1, more preferably about 0.75:1 to about 0.95:1, and still more preferably from about 0.8:1 to 0.9:1. In an aspect of the present invention, the height 254a of the slit 252 may be about 8 mm to about 15 mm, more preferably about 7 mm to about 13 mm, and still more preferably about 8 mm to about 10 mm. The height may be optimized based upon the size of the container. The ratio of the width 256a of the slit 252 to the height 254a of the slit 252, prior to actuation, may be from about 8:1 to about 14:1, more preferably about 9:1 to about 13:1, and still more preferably about 12:1. For example the width 256a of the slit 252 may be from about 0.25 mm to about 1.5 mm, more preferably about 0.5 mm to about 1.0 mm, and still more preferably about 0.80 mm to about 0.85 mm.

The valve 250 may comprise a material with sufficient strength and elasticity such that applying a force onto the valve 250 in a direction parallel to the height of the slit 252 (i.e., in a direction perpendicular to the longitudinal axis of the body 100 along the height of the body) will cause the two opposing valve portions 251, 253 to move away from each other, thereby widening the slit 252. That is, the two opposing valve portions 251, 253 move in a direction perpendicular to the height of the slit 252 and perpendicular to the longitudinal axis of the of body 100 (i.e., in a direction along the width of the body 100 toward the inner surface of the body), thereby expanding the slit 252 (FIG. 3B). The material may also have sufficient strength and elasticity such that once the force is removed the valve portions 251, 253 retract in a direction opposite to the stretching direction, i.e., in a direction along the width of the body toward the center of the body 100 (FIG. 3C). For example, the valve 252 may have a Shore durometer from about 40 A to about 60 A. In an aspect, the valve may comprise a material having a Shore durometer of about 40 A. In another aspect, the valve may comprise a material having a Shore durometer of about 60 A. The material may comprise silicone, for example.

As shown in FIG. 3B, in the actuated state, i.e., when compressive force has been applied to the valve 250, the width 254b and height 256b of the slit 252 are altered as compared to width 254a and height 256a in the non-activated state. Specifically, the height 254b may be smaller than the height 254a, while the width 256b is many times larger than the width 256a, in particular at a midway point along the height 254b. For example the ratio of the height 254a to the height 254b may be from about 1:0.7 to about 1:0.9, preferably about 1:0.75 to about 1:0.85, more preferably about 1:0.8. The ratio of the width 256a to the width 256b (at the midpoint of the height 254b) may be from about 1:2 to about 1:10, preferably about 1:4 to about 1:8, and still more preferably about 1:6. As shown in FIG. 3B, in the actuated state, the slit 252 width is greatest at the midpoint of the height 256a and gradually decreases/tapers toward the top and bottom of the slit 252. In an example aspect, the height 254b may be from about 6 mm to 9 mm, more preferably about 6.5 mm to about 8.5 mm, still more preferably 7.0 mm to about 8.0 mm, and most preferably about 7.75 mm. In an example aspect, the width 256b may be from about 1.5 mm to about 4 mm, more preferably about 2.0 mm to about 3.5 mm, and still more preferably about 3.5 mm.

As shown in FIG. 3C in the released state, i.e., when the compressive force has been removed from the valve 250, the height 254c and the width 256c of the slit 252 return to sizes close to the sizes of the height 254a and width 256a prior to actuation. However, as shown FIG. 3C, due to the initial dimensions of the slit 252 (as shown in FIG. 3A) and the elastic and hardness properties of the materials, the height 254c will remain slightly smaller than the height 254a and the width 256c will remain slightly larger than the width 256a. For example the ratio of the height 254a to the height 254c may be from about 1:85 to about 1:0.95, more preferably about 1:0.9. The ratio of the width 256a to the width 256c may be from about 1:1.25 to about 1:3, more preferably about 1:1.5 to about 1:2.50, and still more preferably about 1:2. Because the width 256c remains even after the actuation is removed, there will still be fluid flow after the actuator is released. Thus, the valve 252 allows for increased and reduced fluid flow rate, but does stop the flow of fluid.

Activation of the applicator to release the solution and control the flow may be achieved by one handed actuation of the actuator 150. To operate the applicator, the operator first grasps the tube 100 and the actuator 150. Prior to applying compressive force on the actuator 150, the valve 250 is in the pre-actuated configuration shown in FIG. 3A. When the operator desires to release the fluid contained in the container 300, the operator begins to compress the actuator 150 toward the body 100 by applying a compressive force onto the actuator 150. As the actuator 150 begins to move toward the body 100, the first contact point 152 begins to apply pressure on the body 100. This pressure then applies pressure on the valve 250 that is located directly adjacent to or sufficiently near the first contact point 152. As the operator continues to press the actuator 150 the pressure continues to increase on the valve 250, thereby increasing the width and decreasing the height of the slit 252. Upon further actuation of the actuator 150 the second contact point 154 begins to contact the body 100. By this point, the valve 250 will be in the actuated state shown in FIG. 3B.

The operator then continues to compress the actuator 150 imparting pressure on the body 100 via the second contact point 154. Once sufficient compressive force is imparted at the second contact point 154, container 300 fractures, thereby releasing flow of the fluid contained therein. The solution will drain from the container 300 into the fluid chamber 160 under its own weight. After passing through the pledget 170 and becoming tinted, the fluid flow passes through the open slit 252. If the operator continues to apply pressure on the actuator 150, the continued pressure at the first contact point 152 will cause the valve slit 252 to remain fully actuated as shown in FIG. 3B, thereby providing maximum flow rate. However, because the valve 250 biases toward the position shown in FIG. 3C, the operator can control the flow of fluid through the valve 250 by removing the compressive force from the actuator 150. As the operator removes the compressive force from the actuator 150, the pressure at the first contact point 152 will decrease and the elastic property of the valve 250 will cause the slit width to decrease and the height to increase. When the operator totally releases the compressive force on the lever 150, the slit 252 will have the configuration shown in FIG. 3C, thereby greatly reducing the flow rate as compared to that configured of FIG. 3B. The operator may alternate between actuating and releasing the actuator 150 to switch between maximum flow rate (FIG. 3B) and minimum flow rate (FIG. 3C). Thus, the applicator 10 allows the operator to easily control the initial and continued release of fluid and the flow rate of fluid with one hand. As noted above, because the width 256c remains after releasing the actuator, there will still be a minimum flow rate when the actuator is released.

Figure 4A:
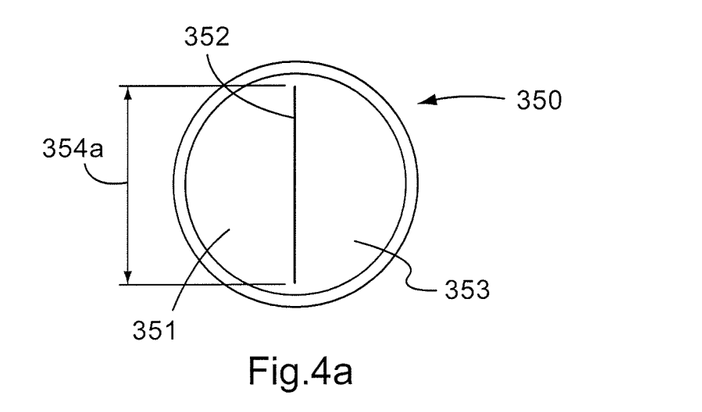
FIG. 4A is a front view of a valve in a pre-actuated configuration in accordance with other aspects of the present invention.
Figure 4B:
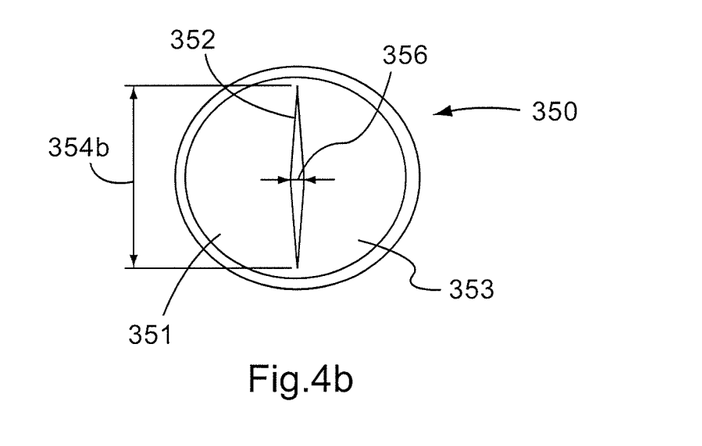
FIG. 4B is a front view of the valve of FIG. 4A in an actuated configuration.

FIGS. 4A and 4B show a valve 350 in accordance with another aspect of the present invention. The valve 350 differs from the valve 250 in that the valve 350 provides an on/off configuration. In particular, when using the valve 350, actuation of the actuator will allow for fluid flow, but when the actuator is released, the valve 350 will substantially close, thereby substantially stopping the flow of fluid (as opposed to merely reducing the fluid flow rate). The valve 350 may be used in the applicator 10 in the same manner and in the same position/orientation as shown in FIG. 2, and as discussed above with respect to the valve 250. The valve 350 may include a slit 352 separating the valve into two opposing portions 351, 353. Thus, the valve 350 is bifurcated. The valve 350 may be similarly configured to open when pressure is applied to the outer circumference of the valve 350. FIGS. 4A and 4B show the same views as shown in FIGS. 3A and 3B, respectively. That is, FIGS. 4A and 4B show front views of the valve 350 (i.e., the views show the surface of the valve that faces the application member 200). FIG. 4A shows a front view of the valve 350 prior to actuation of the actuator 150, i.e., prior to the application of any compressive force. FIG. 4B shows a front view of the valve 350 during maximum actuation of the actuator 150, i.e., during maximum application of compressive force.

The orientation of the slit 350 and the height 354a of the slit 352 in the pre-actuated state is the same as in the slit 250 shown in FIG. 3A. The width of the slit 352, however, is different. As shown in FIG. 4A, in the pre-actuated state, the opposing portions 351, 353, may be substantially flush against each other. Thus, the width of the slit may be substantially 0 (zero).

The valve 350 may comprise a material with sufficient strength and elasticity such that applying a force onto the valve 350 in a direction parallel to the height of the slit 352 (i.e., in a direction perpendicular to the longitudinal axis of the body 100 along the height of the body) will cause the two opposing valve portions 351, 353 to move away from each other, thereby widening the slit 352. That is, the two opposing valve portions 351, 353 move in a direction perpendicular to the height of the slit 352 and perpendicular to the longitudinal axis of the of body 100 (i.e., in a direction along the width of the body 100 toward the inner surface of the body), thereby expanding the slit 352 (FIG. 4B). The material may also have sufficient strength and elasticity such that once the force is removed the valve portions 351, 353 retract in a direction opposite to the stretching direction, i.e., in a direction along the width of the body toward the center of the body 100. For example, the valve 352 may have a Shore durometer from about 40 A to about 60 A. In an aspect, the valve may comprise a material having a Shore durometer of about 40 A. In another aspect, the valve may comprise a material having a Shore durometer of about 60 A. The material may comprise silicone, for example.

As shown in FIG. 4B, in the actuated state, i.e., when compressive force has been applied to the valve 350, the width 356 and height 354b of the slit 352 are altered as compared to width and height 354a in the non-activated state. Specifically, the height 354b may be smaller than the height 354a, and while there is no slit width prior to actuation, there is a slit width 354b during actuation. For example the ratio of the height 354a to the height 354b may be from about 1:0.7 to about 1:0.9, preferably about 1:0.75 to about 1:0.85, more preferably about 1:0.8. Because the width of the slit 352 in the pre-actuated state is essentially 0 (zero), a relative ratio between a pre-actuated width and actuated width is not determinable. However, a ratio of the width 356 to a ratio of the height 354b may be about 1:10 to about 1:15, more preferably about 1:11 to about 1:14, still more preferably 1:12 to about 1:13. In an example aspect, the height 354b may be about 7 mm to about 10 mm, more preferably about 7.5 mm to about 9.5 mm, still more preferably 8.0 mm to about 9.0 mm, and most preferably about 9.0 mm. In an example aspect, the width 356 may be from about 0.50 mm to about 1.0 mm, more preferably about 0.7 mm to about 0.9 mm, and still more preferably about 0.8 mm.

In the released state, i.e., when the compressive force has been removed from the valve 350, the height and the width of the slit 352 return to sizes very close to the sizes of the height and width of the slit 352 prior to actuation. For example the ratio of the height 354a to the height after compressive force is removed is substantially 1:1. Similarly, the width of the slit 352 after compressive force is removed is essentially 0 (zero). That is, when the compressive force is removed, the two valve portions 351, 353 may be substantially flush against each other. The released state of the slit 352 appears substantially the same as shown in FIG. 4A. The valve 350 provides different flow control as compared to the valve 250 because of the smaller initial slit width and because the valve closes when compressive force is removed. Operation of the actuator to actuate the valve and release solution from the container is the same as discussed above. The valve 350 thus provides an "on/off" control because the slit 352 returns to an approximately flush state (i.e., the width of the slit 352 is about or near 0 (zero)) after the compressive force is removed. By using an applicator having the valve 350, the operator can allow fluid flow (i.e., "on") by actuating the actuator and reduce the fluid flow to about or near zero (i.e., "off") by removing actuation of the actuator.

The solution may then soak into, or otherwise flow through, the application material 200 at an operator controlled rate. The fluid chamber 160 may serve to accumulate and distribute the solution evenly over substantially the entire area of the application material 200. Once the application material 200 is engorged, for example, the solution may then be applied to a patient by wiping the distal surface of the application material 200 against the skin.

While the above valve and related features have been described with respect to the applicator 10 shown herein, it should be understood that the applicator may include any non-mutually exclusive features described in a variety of known applicators. For example, the applicator could include a dual ampoule arrangement such as described in U.S. Pat. No. 7,182,536. Other relevant features can be found in U.S. Patent Application Publication Nos. 2012/0003029; 2011/0319842; 2008/0298879; 2008/0292383; 2007/0231051; 2007/0248399; 2006/0039742; 2010/0168638; 2010/0168637; 2002/0076258; 2008/0219750; 2010/0286637; 2011/0066121; 2011/0245784; and U.S. Pat. Nos. 7,422,388; 7,241,065; 6,991,394; 6,991,393; 6,536,975; 6,533,484; 5,772,346; 5,690,958; 5,538,353; 5,445,462; 4,415,288; 4,498,796; 5,769,552; 6,488,665; 7,201,525; 3,757,782; 5,288,159; 5,308,180; 5,435,660; 5,445,462; 5,658,084; 5,772,346; 5,791,801; 5,927,884; 6,371,675; 6,916,133; 6,371,675; 7,866,471; 7,946,779; and 8,118,766. Each of the above listed publications and patents are hereby expressly incorporated by reference herein.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but is to be accorded the full scope consistent with the language claims, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. An applicator assembly comprising:
   a body having a proximal end portion and a distal end portion;
   an actuator operatively coupled to the body;
   a container disposed within the body;
   an application member attached to the distal end portion; and
   a valve disposed between the container and the application member, the valve comprising an outer circumference,
   wherein actuation of the actuator imparts compressive force on the outer circumference of the valve and on the container sufficient to open the valve and fracture the container, thereby placing the interior of the container in fluid communication with the application member, and
   wherein the actuator is also configured to open the valve without fracturing the container.

2. The applicator assembly of claim 1,
   wherein the actuator comprises a first contact point and a second contact point, and
   wherein the actuator is configured such that each contact point contacts the body upon actuation of the actuator.

3. The applicator assembly of claim 2,
   wherein the actuator is configured such that the first contact point imparts compressive force on the valve upon actuation of the actuator.

4. The applicator assembly of claim 3,
   wherein the actuator is configured such that the second contact point imparts compressive force on the container upon actuation of actuator.

5. The applicator assembly of claim 4,
   wherein the actuator is configured such that during actuation of the actuator the first contact point imparts compressive force to the valve prior to the second contact point imparting compressive force to the container.

6. The applicator assembly of claim 3, wherein the valve comprises a slit separating the valve into first and second valve portions.

7. The applicator assembly of claim 6, wherein the compressive force is imparted in a direction parallel with a height of the slit.

8. The applicator assembly of claim 6,
   wherein the valve is configured such that the first and second valve portions move away from each other upon application of the compressive force.

9. The applicator assembly of claim 8,
   wherein the valve is configured such that the first and second valve portions move toward each other upon removal of the compressive force.

10. The applicator assembly of claim 1, wherein the valve comprises a Shore durometer from about 40 A to about 60 A.

11. The applicator assembly of claim 1, further comprising a pledget disposed between the valve and the container.

12. The applicator assembly of claim 11, wherein the pledget comprises a hydrophobic material.

13. The applicator assembly of claim 11, wherein the pledget is impregnated with at least two dyes, wherein the at least two dyes have different solubilities relative to a solution contained in the container.

14. A method of applying a solution to a surface comprising:
    providing an applicator assembly having:
        a body having a proximal end portion and a distal end portion;
        an actuator operatively coupled to the body;
        a container disposed within the body;
        an application member attached to the distal end portion; and
        a valve disposed between the container and the application member, the valve comprising an outer circumference;
    actuating the actuator, wherein actuation of the actuator applies a compressive force to the outer circumference of the valve and on the container sufficient to open the valve and fracture the container, thereby placing the interior of the container in fluid communication with the application member; and
    contacting the application member to the surface, thereby applying the solution to the surface,
    wherein the actuator is also configured to open the valve without fracturing the container.

15. The method of claim 14,
    wherein the actuator comprises a first contact point and a second contact point, and
    wherein actuating the actuator comprises contacting each contact point with the body.

16. The method of claim 15,
    wherein actuating the actuator comprises imparting compressive force on the valve via the first contact point.

17. The method of claim 16,
    wherein actuating the actuator comprises imparting compressive force on the container via the second contact point.

18. The method of claim 17,
    wherein actuating the actuator comprises imparting compressive force on the valve prior to imparting compressive force on the container.

19. The method of claim 14,
    wherein the valve comprises a slit separating the valve into first and second valve portions, and
    wherein actuating the actuator causes the first and second valve portions to move away from each other.

20. The method of claim 19,
    further comprising discontinuing actuation of the actuator,
    wherein discontinuing actuation of the actuator causes the first and second valve portions to move toward each other.

21. The method of claim 19, wherein the compressive force is imparted in a direction parallel with a height of the slit.

22. The method of claim 14,
    wherein actuating the actuator comprises compressing the actuator toward the body.

23. The method of claim 14,
    further comprising discontinuing actuation of the actuator, thereby reducing or substantially terminating a flow rate of solution to the application member.

24. The method of claim 14,
wherein the applicator further comprises a pledget disposed between the valve and the container,
wherein the pledget is impregnated with at least two dyes, and
wherein the at least two dyes have different solubilites relative to the solution,
the method further comprising drying the solution after the solution is applied to the surface, thereby producing a colored deposit on the surface,
wherein the color of the deposit changes as the solution dries.

\* \* \* \* \*